US008835000B2

(12) United States Patent
Natarajan et al.

(10) Patent No.: US 8,835,000 B2
(45) Date of Patent: Sep. 16, 2014

(54) HIGH-DENSITY FLUORESCENT DYE CLUSTERS

(75) Inventors: Arunkumar Natarajan, Niskayuna, NY (US); Andrew Arthur Paul Burns, Niskayuna, NY (US); Sumeet Jain, Schenectady, NY (US); Patrick Joseph McCloskey, Watervliet, NY (US)

(73) Assignee: General Electric Company, Niskayuna, NY (US)

( * ) Notice: Subject to any disclaimer, the term of this patent is extended or adjusted under 35 U.S.C. 154(b) by 166 days.

(21) Appl. No.: 13/336,376

(22) Filed: Dec. 23, 2011

(65) Prior Publication Data

US 2013/0164531 A1 Jun. 27, 2013

(51) Int. Cl.
 *B32B 5/16* (2006.01)
 *C09B 69/10* (2006.01)
 *B82Y 5/00* (2011.01)

(52) U.S. Cl.
 USPC ............... 428/402; 525/326.6; 525/326.7; 525/327.2; 977/773; 977/902

(58) Field of Classification Search
 None
 See application file for complete search history.

(56) References Cited

U.S. PATENT DOCUMENTS

| 5,298,583 A | 3/1994 | Heiliger et al. |
| 6,060,598 A | 5/2000 | Devlin et al. |
| 7,087,744 B2 | 8/2006 | Nishigaki et al. |

| 2009/0035576 A1 | 2/2009 | Prasad et al. |
| 2010/0104585 A1 | 4/2010 | Kiessling et al. |
| 2011/0059867 A1 | 3/2011 | Kim et al. |
| 2011/0118459 A1 | 5/2011 | Smith et al. |

FOREIGN PATENT DOCUMENTS

| EP | 0513560 A1 | 11/1992 |
| EP | 2366785 A1 | 9/2011 |
| WO | 2009078970 A1 | 6/2009 |

OTHER PUBLICATIONS

Lim et al. Chem. Mater. 2009, 21, 5819-5825.*
Tang et al. Chem. Commun. 2009, 4974-4974.*
Lu et al. J. Mater. Chem. 2012, 22(19), 9890-9900.*
Hong, Yuning, et al. "Label-Free Fluorescent Probing of G-Quadruplex Formation and Real-Time monitoring of DNA Folding by a Quaternized Tetraphenylethene Salt with Aggregation-Induced Emission Characteristics", Chemistry, A European Journal, vol. 14, Issue 21, pp. 6428-6437, Jul. 18, 2008.
Qin, Anjun, et al. "Luminogenic Polymers with Aggregation-Induced Emission Characteristics", Progress in Polymer Science, Aug. 25, 2011.
Liu, Jianzhao, et al., "Aggregation-Induced Emission of Silole Molecules and Polymers: Fundamentals and Applications", Journal of Inorganic and Organometallic Polymers and Materials, vol. 19, Issue 3, pp. 249-285, May 16, 2009.
Wang, Bing, "Starburst Triarylamine Donor-Acceptor-Donor Quadrupolar Derivatives Based on Cyano-Substituted Diphenylaminestyrylbenzene: Tunable Aggregation-Induced Emission Colors and Large Two-Photon Absorption Cross", Chemistry—A European Journal, vol. 17, Issue 9, pp. 2647-2655, Feb. 25, 2011.

(Continued)

*Primary Examiner* — Vu A Nguyen
(74) *Attorney, Agent, or Firm* — Eileen B. Gallagher

(57) ABSTRACT

The present invention relates to modular sterically enhanced emission dye (SEED) clusters, wherein multiple SEED molecules are appended to a single polymeric chain.

21 Claims, 2 Drawing Sheets

(56) References Cited

OTHER PUBLICATIONS

Jiang, Yihua, et al., "Multibranched Triarylamine Endcapped Triazines with Aggregation-Induced Emission and Large Two-Photon Absorption Cross-Sections". Chemical Communications, vol. 26, pp. 4689-4691, 2010.

Lu, Hongguang, et al., "A Series of Poly[N-(2-Hydroxypropyl)methacrylamide] Copolymers with Anthracene-Derived Fluorphores Showing Aggregation-Induced Emission Properties for Bioimaging", Journal of Polymer Science Part A: Polymer Chemistry, Nov. 7, 2011.

Search Report and Written Opinion from corresponding PCT Application No. PCT/EP2012/076248 dated Apr. 17, 2013.

* cited by examiner

HIGH-DENSITY FLUORESCENT DYE CLUSTERS

BACKGROUND

Fluorescent dyes are widely used in biological assays (e.g., DNA and protein microarrays, DNA/RNA/Protein blotting, etc.), imaging (confocal, epifluorescence, pathology, live- and fixed-cell in vitro, whole-body in vivo, etc.) and diagnostics (e.g., in vitro diagnostics, sandwich assays, lateral flow assays). Enhancement of the signal strength of the fluorescent dye would be beneficial for the such uses of fluorescence, either for enhancing sensitivity (e.g., finding low-abundance target molecules) or increasing throughput (e.g., decreased integration time for imaging). The simplest approach to increasing signal strength is to increase the fluorophore concentration. However, this approach is generally not possible for conventional fluorescent dyes because the dye molecules interact electronically with each other and quench the signal at high concentrations. This is the case both for free dyes in solution as well as dyes bound to biomolecules or surfaces. Thus, any signal gain is offset by signal loss due to quenching at high enough local concentrations (e.g., multiple dyes on a single antibody). Another deficiency of traditional fluorescent dyes includes photobleaching, or photo-oxidation of the dye to a non-fluorescent form by the light source, which results in dye degradation and loss of fluorescent signal. Rates and modes of photobleaching are often affected by interactions with solvent molecules, such as water. Photobleaching limits dye longevity under illumination, which detrimentally affects the imaging or detection of the substrate when long integration times or images at multiple timepoints are required.

Therefore, as a result of these shortcomings of traditional fluorescent dyes, a need exists for new fluorescent dyes that can generate strong, long-lasting signals.

SUMMARY OF THE INVENTION

The present invention relates to modular sterically-enhanced emission dye (SEED) clusters, wherein multiple SEED molecules are appended to a single polymeric chain. The present clusters circumvent dye quenching at high dye density, thus enabling higher dye densities and higher signal strength as a function of the number of dyes appended to the chain (e.g., >10× individual fluorophores). Photobleaching and oxidative damage are also minimized by the core-shell architecture of the water-soluble dye clusters which limits dye-solvent interactions.

DETAILED DESCRIPTION OF THE INVENTION

Figure 1:
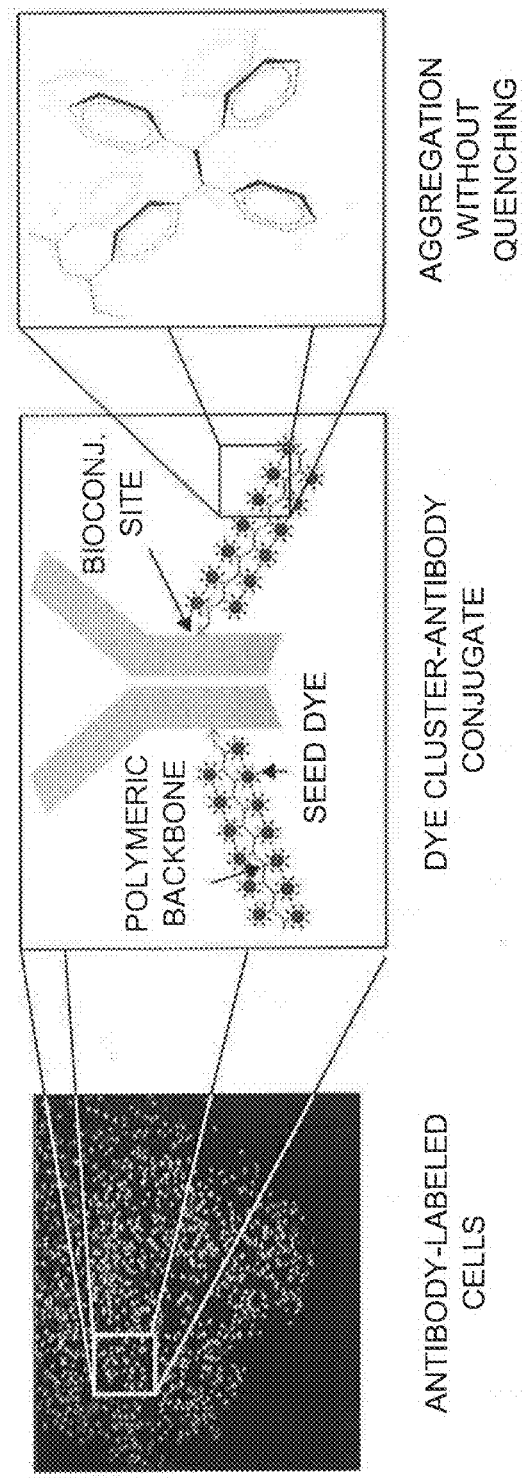
FIG. 1 is a schematic of one embodiment of a SEED cluster for cellular labeling (left) showing a biomolecule (Antibody, center) conjugated to a chain of SEED fluorophores bound to a common backbone (right).

The present clusters described herein avoid several of the key disadvantages of conventional fluorescent dyes. One advantage is that per-cluster brightness is increased because multiple dye molecules are incorporated into a single cluster. The cluster contains a conjugation site for attachment to a biological molecule or other host, such that the cluster may be attached in the same way as a conventional fluorophore. In addition, the photostability of the present clusters is improved in two ways. First, the present dye molecules are relatively hydrophobic, and exist in aqueous solution in an aggregated state, which renders the dye molecule less susceptible to solvent-mediated photo-oxidation reactions. Second, the incorporation of multiple dye molecules in a single cluster ensures that in the event of stochastic blinking or photobleaching of a single dye within the cluster, the cluster as a whole will simply decrease slightly in brightness, rather than disappearing completely (as is the case for conventional fluorophores), enabling targets labeled with the cluster to remain visible for imaging or detection.

Another advantage of the present dye cluster includes their modular nature, which enables integration of different functionalities in a controlled manner to generate multifunctional probes. For example, incorporation of photostabilizing moieties would enhance longevity, incorporation of environmentally responsive moieties would enable sensing and small molecule targeting agents would enhance specificity. Incorporation of a wide variety of dyes is contemplated to create differentiation and enhance signal intensity, while maintaining the known optical and chemical properties of those dyes. The resulting properties of these modular clusters facilitate workflow and improve assay outcomes.

The dye molecules used in the present invention include any dye that can be characterized as a "sterically enhanced emission dye" (SEED) or, alternatively, "aggregation-induced emitter" (AIE). SEEDS are a class of dyes that exhibit a non-linear increase in fluorescence quantum yield with increased dye concentration, but without signal loss due to quenching as seen in traditional dyes. (See Y. Hong, J. Lam, B. Z. Tang, "Aggregation-Induced Emission: Phenomenon, Mechanism and Applications", ChemComm, 2009, 4332-4353, the teachings of which are incorporated herein by reference) Without wishing to be bound by theory, a SEED molecule generally contains substituents which are conjugated to the fluorescent center of the molecule, but which are capable of rotation around a bond axis. As free dyes in solution, this rotation creates a non-radiative decay channel for the energy absorbed by the dye, thereby causing the dyes to be virtually non-fluorescent when free in solution. When the intramolecular rotation is hindered either by interaction with neighboring dye molecules or encapsulation in a rigid matrix, the fluorescence quantum yield of the molecules increases dramatically, while the pendant groups prevent electronic interactions with adjacent dyes, enabling the dye molecules to emit without quenching. Unless otherwise stated, reference made herein to a "dye" means a dye that could be classified as a SEED molecule.

The clusters described herein include multiple SEED molecules bound onto some of the monomer units of the polymer. Due to the hydrophobicity of the SEED molecules, under aqueous conditions, they will tend to avoid interactions with water, thereby forming a cluster bound together by hydrophobic interactions. The cluster formation brings the SEED molecules into molecular contact with each other, which suppresses the rotational (non-radiative) decay mode of the dyes and generates a dense cluster of dye molecules, each independently emitting at (or near) their peak quantum efficiency. Attachment of multiple SEED molecules to a single polymer backbone enables very high local dye density to be achieved, thus allowing, for example, tens of dye molecules to be bound to a biomolecule. In contrast, conventional technologies are generally limited to 1-3 dye molecules per biomolecule before dye quenching begins to limit the gain in signal.

The present clusters are advantageous over SEED-polymers synthesized to date. SEED polymers are generally large molecular weight polymers that are not water-soluble. Moreover, the fluorescent properties of such SEED-polymers need to be induced by first dissolving the SEED-polymer in a solvent (e.g. a non-aqueous solvent such a THF), and then inducing aggregation of the SEED-polymers by increasing the concentration of a non-solvent in which the SEED-polymer is not soluble (e.g. water). This aggregation into particles causes the fluorescence of the SEED-polymers. ((See C-T. Lai, J-L. Hong, "Aggregation Induced Emission in Tetraphenylthiophene-derived organic molecules and vinyl polymer" J. Phys. Chem. B, 2010, 114, 10302-10310 and A. Qin et al. "Luminogenic polymers with aggregation-induced emission characteristics," Progress in Polymer Science, 37 (2012) 182-209, the entire teachings of both are incorporated herein by reference). In contrast, the present clusters are low molecular weight, water-soluble and are able fluoresce without altering the solvent mixture.

An embodiment of the invention includes a cluster comprising a polymer backbone comprising two or more optionally substituted monomer units; a solubilizing agent; a conjugation site; and a multiplicity of sterically enhanced emission dye molecules disposed along the polymer backbone.

An embodiment of the invention includes a sustained emission high density luminescent cluster comprising a polymer backbone comprising two or more optionally substituted monomer units; a solubilizing agent; a conjugation site; and a multiplicity of sterically enhanced emission dye molecules disposed along the polymer backbone such that rotational decay is suppressed and emission is sustained in aqueous solution.

An embodiment of the invention includes a sustained emission high density luminescent cluster, corresponding to:

$[B]_v[S—B—F]_w[B—F]_x[B—S]_y[B—C]_z$, wherein

B is the optionally substituted monomer unit;
S—B—F is the monomer unit with sterically enhanced emission dye and a solubilizing agent attached
B—F is the monomer unit with sterically enhanced emission dye attached;
B—S is the monomer unit with the solubilizing agent attached;
B—C is the monomer unit with a conjugation site attached;
v+w+x+y+z is between 3 and 100 and w+x is greater than or equal to 3.

In a preferred embodiment, v+w+x+y+z is between 5 and 80, and w+x is greater than or equal to 3, in a more preferred embodiment, v+w+x+y+z is between 15 and 50 and w+x is greater than 10. "Sustained emission" means the retention of fluorescent properties without significant loss of signal due to bleaching or oxidation.

A "cluster" means a compound that includes at least two SEED molecules, a solubilizing agent and a bioconjugation site attached to a polymeric backbone.

"High density" means the cluster includes more than one SEED molecule. In at least one embodiment, the cluster includes 2, 3, 4, 5, 6, 7, 8, 9, 10, 11, 12, 13, 14, 15, 16, 17, 18, 19, or 20 dye molecules. In at least one embodiment, the cluster includes 10, 11, 12, 13, 14, 15, 16, 17, 18, 19, or 20 dye molecules. In at least one embodiment, the cluster includes between 10 and 50 dye molecules. The dye molecules may be the same or different. A "luminescent cluster" means the cluster emits light through fluorescence or phosphorescence.

A "polymer" is a compound that comprises monomer units that may be the same or different from each other. In at least one embodiment, the polymer is comprised of 3 to 100 monomer units. In a specific embodiment, the polymer is comprised of 10 to 50 monomer units. Hydrodynamic diameter can also be used to define the size of a polymer. As used herein, the "hydrodynamic diameter" of the polymer is the effective diameter of the polymer in a liquid, preferably aqueous, environment, assuming that the polymer forms a spherical object in solution. Hydrodynamic diameter may be measured by various techniques known to those skilled in the art including dynamic light scattering (DLS) and/or fluorescence correlation spectroscopy (FCS). The hydrodynamic diameter of a polymer will vary with the type and ordering of the monomers constituting the polymer. As such, even polymers with the same number of monomers may have a different hydrodynamic diameter depending upon composition. In at least one embodiment, the hydrodynamic diameter of the compound is less than 100 nm. In a specific embodiment, the hydrodynamic diameter of the compound is 2-15 nm.

The polymer can include the same monomer units, or may include different monomer units. In either case, the monomer units are formed from a group selected from an alkenyl (for example, vinyl), an acrylate (for example acrylate, methacrylate, or alkyl methacrylate), an ether (for example, an epoxide, etc.), an amine (for example, urethane, nylon-type polymerizations, etc.) or any combination thereof. In a specific embodiment, the monomer unit is formed from the group selected from acrylate, methylacrylate, vinyl, urethane, epoxide or a combination thereof.

In at least one embodiment, the dye and the solubilizing agent are attached to the same monomer unit. Alternatively the dye and the solubilizing agent are attached to different monomer units. In at least one embodiment, the polymer formed can be formed from monomer units that include both the dye and the solubilizing agent; from monomer units that include the dye and separately, or a combination of thereof. In a further embodiment, the polymer also includes optionally substituents that include The monomer units, including those represented by [B], may be optionally substituted with one or more substituents. These optionally substituents can be attached to monomer units that also include a solubilizing agent, a dye or both. Suitable substituents for the monomer units include alkyl (for example, methyl, ethyl, propyl, i-propyl, butyl, sec-butyl, isobutyl and tert-butyl), alcohols (e.g., hydroxymethyl, hydroxyethyl, hydroxypropyl, oligo(alkyl alcohols), etc.), oligomeric ethers (e.g., oligo(ethylene oxide), oligo(propylene oxide), etc.), salts (e.g., ammonium chloride, ammonium bromide, sodium sulfonate, etc.), amines (aminomethyl, aminoethyl, aminopropyl, etc.), sulfates, sulfonates, phosphates, phosphonates, carboxylates, ketones, aldehydes, azides, thiols, amines (primary, secondary or tertiary), alkenes, alkynes, esters or combinations thereof. Another class of optional substituents that can be incorporated either off of a monomer unit or at one of the terminal caps of the cluster includes photostablizers, environmentally responsive moieties, and/or a small molecule targeting agents. Such substituents can be present as the only attachment to the monomer unit or many be attached to a monomer unit that includes as of the other monomer attachments described herein (e.g. dye, solubilizing agent, etc.)

Photostabilizers, which act to prevent photobleaching by preventing the creation of or decreasing the concentrations of photoreactive species such as radicals or singlet oxygen. As used herein, "photostabilizers" include radical scavengers, singlet oxygen scavengers, etc. Included in this class are radical scavengers (e.g., (2,2,6,6-tetramethylpiperidin-1-yl) oxidanyl, TEMPO) and singlet oxygen scavengers (e.g., α-tocopherol, etc.). In a specific embodiment, the optionally substituted monomer B comprises a photostabilizing moiety such as a radical scavenger, triplet quencher or singlet oxygen scavenger. In a specific embodiment, the optionally substituted monomer comprises a photostabilizing moiety such as a radical scavenger, triplet quencher or singlet oxygen scavenger.

An "environmentally response moiety" enables sensing of chemical analytes or physical variables such as pH or temperature in the environment of the cluster.

A "small molecule targeting agent" enhances specificity of the cluster.

An "aqueous solubilizing agent" or a "solubilizing agent" is a moiety that enhances the aqueous solubility of the substrate to which it is attached. In at least one embodiment, the solubilizing agent is attached, specifically covalently attached, to the polymer at one or more or the monomer units of the polymer.

Within a given cluster, the solubilizing agents may be the same or may be different. A solubilizing agent is selected from hydrophilic sterically repulsive groups (for example, oligo(ethylene glycol), oligosaccharides, etc.), cationically charged groups (for example, amines), anionically charged groups (for example, sulfonates, carboxylic acids, phosphonates, phosphates, etc.) and zwitterionically charged groups (e.g., amino-phosphonates, amino-sulfonates, such as N,N-dimethyl-N-acryloyloxyethyl-N-(3-sulfopropyl)-ammonium betaine, N,N-dimethyl-N-acrylamidopropyl N-(3-sulfopropyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate, 2-methacryloyloxyethyl phosphorylcholine (MPC), 2-[(3-acrylamidopropyl)dimethylammonio]ethyl 2'-isopropyl phosphate (AAPI), 1-vinyl-3-(3-sulfopropyl)imidazolium hydroxide, 1-(3-sulfopropyl)-2-vinylpyridinium betaine, N-(4-sulfobutyl)-N methyl-N,N-diallylamine ammonium betaine (M DABS), N,N-diallyl-N-methyl-N-(2-sulfoethyl) ammonium betaine, N,N-dimethyl-N-(3-methacrylamidopropyl)-N-(3-sulfopropyl) ammonium betaine, N,N-dimethyl-N-acryloyloxyethyl-N-(3-sulfopropyl)-ammonium betaine, N,N-dimethyl-N acrylamidopropyl-N-(2-carboxymethyl)-ammonium betaine, N,N-dimethyl-N-methacryloyloxyethyl-N-(3-sulfopropyl)-ammonium betaine, and N, N-dimethyl-N-(3-methacrylamidopropyl)-N-(3-sulfopropyl) ammonium betaine) or combinations thereof.

In at least one embodiment, each sterically enhanced emission dye is independently attached to the one or more monomer units either directly or through a linker. The linker moiety may be any bi- or poly-functional group which enables the covalent linkage of the dye moiety to the monomer. Specifically, linker moieties may contain alkyl chains, alkylene oxide chains (e.g. ethylene oxide/ethylene glycol), and appropriate functionalities for dye conjugation (e.g., amine, thiol, alkene, alkyne, azide, bioconjugate chemistry groups, etc.). In a preferred embodiment, the linker chemistry is bifunctional (i.e. reactive towards the monomer and towards the dye) and hydrophobic. In an alternative embodiment, the linker is polyfunctional (e.g., tri-functional or tetra-functional) containing multiple binding sites for SEED molecule attachment and at least one site for monomer-attachment. In a further alternative embodiment, the linker is polyfunctional and contains multiple binding sites for both SEED molecules and monomers, enabling monomer cross-linking following SEED cluster synthesis. The linker used to attach the dye molecule to a monomer of the polymer may be the same or different as the linker used to attach the conjugation site to the polymer. In a further alternative embodiment, the polyfunctional linker contains multiple different ligation chemistries to enable the attachment of different SEED molecules at specified ratios (2:1, 1:1, 3:1 etc.) based on the use of specific chemistries to covalently attach each type of dye molecule to the SEED cluster.

The per-cluster brightness and size (i.e. hydrodynamic diameter) may be tailored by changing the number of dye-monomer units used, and the absorption and emission wavelength may be tuned by appropriate choices of dye. In at least one embodiment, each sterically enhanced emission dye within the cluster is the same. Alternatively, at least two or more different sterically enhanced emission dyes are within the cluster. In a specific embodiment, the different sterically enhanced emission dyes have different absorption and/or emission wavelengths.

A wavelength refers to either the absorption or excitation wavelength of the dye. A wavelength range may encompass both the absorption or excitation wavelength of a single dye or multiple dyes, or can refer to only the absorption or excitation wavelength of a single dye or multiple dyes. Representative wavelengths encompassing both the absorption or excitation wavelength of a single dye or multiple dyes includes from 300 to 800 nm. Specifically, the absorption or excitation wavelength of a single dye or multiple dyes is from 400 to 750 nm. Representative wavelengths encompassing the absorption wavelength of a single dye or multiple dyes includes from 450 to 750 nm. Specifically, the absorption or excitation wavelength of a single dye or multiple dyes is from 450 to 650 nm. Representative wavelengths encompassing the excitation wavelength of a single dye or multiple dyes includes from 380 to 420 nm. Representative wavelengths encompassing the excitation wavelength of a single dye or multiple dyes includes from 450 to 520 nm. Representative wavelengths encompassing the excitation wavelength of a single dye or multiple dyes includes from 500 to 550 nm. Representative wavelengths encompassing the excitation wavelength of a single dye or multiple dyes includes from 600 to 650 nm. Specifically, the absorption or excitation wavelength of a single dye or multiple dyes is from 650 to 800 nm.

The overall properties of the cluster can be modulated through control of the ratios of the different components. In one embodiment, the ratio between different sterically enhanced emission dyes in each cluster is controlled. In a specific embodiment, the two different dyes are present in within the cluster in equal amounts (1:1 ratio). Alternatively, the two dyes are present in ratios of for example, but not limited to, 1:2; 1:3; 1:4 or 1:5. In another embodiment of the invention, the cluster includes two, three, four, or five different sterically enhanced emission dyes. In another embodiment of the invention, the cluster includes four different sterically enhanced emission dyes. In another embodiment of the invention, the cluster includes three different sterically enhanced emission dyes. In another embodiment of the invention, the cluster includes two different sterically enhanced emission dyes. When more than two dyes are present in the cluster the ratio of these dyes can also be controlled. For example, the cluster may contain three different dyes all in equal amounts (e.g. 1:1:1) or in different amounts (e.g. 1:2:1). As such, analogous control of the ratio of dyes in clusters containing more than two dyes is contemplated.

Similarly, the ratio between the sterically enhanced emission dyes, whether the same or different, and the solubilizing agents (whether all the same or different) in each cluster is controlled. In a specific embodiment, the sterically enhanced emission dye and solubilizing agent are present in within the cluster in equal amounts (1:1 ratio). Alternatively, unequal amounts of the sterically enhanced emission dye and solubilizing agent may be present within the cluster. For example, the sterically enhanced emission dye and solubilizing agent may be present in ratios of, for example, but not limited to, 1:2; 1:3; 1:4, 1:5. 1:6, 1:7, 1:8, 1:9 or 1:10. The ratio of the dye to the solubilizing agent depends upon many factors, for example, the overall size of the cluster, the size of the dye, the hydrophobicity of the monomer, or the number of dye molecules in the cluster.

Inclusion of any dye that possesses the properties of SEED molecules may be used in this invention. The underlying fluorophore molecule used to prepare a SEED molecule may be taken from any of the known families of organic fluorophores, for example, cyanines, xanthenes (rhodamines, fluoresceins), boron-dipyrromethenes, boron dipyridyls, naphthalenes, coumarins, acridines, acridiniums, tetrapyrroles, tetraphenylethenes, oxazines, pyrenes, oxadiazoles, subphthalocyanines, carbopyrinins, benzopyriniums, phthalocyanines, etc., and with appropriate functionalization with multiple pendant conjugated groups capable of intramolecular rotation (e.g., phenyl).

Representative SEED molecules include the following:

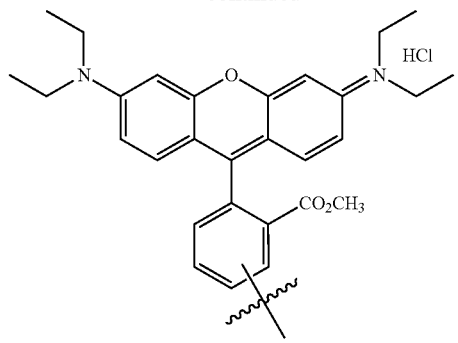

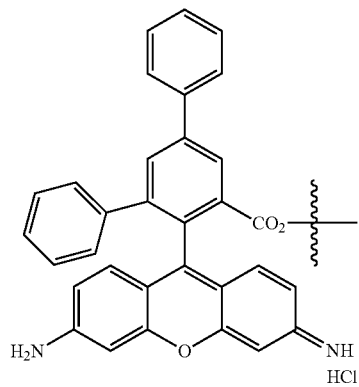

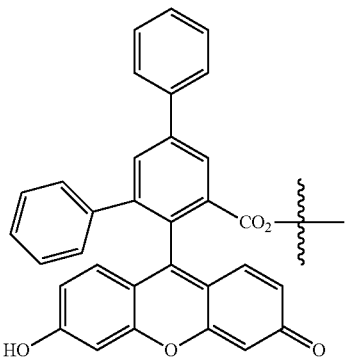

Fluorescein

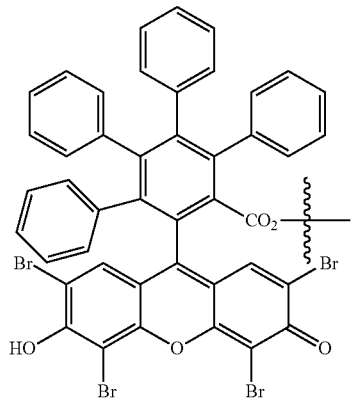

Eosin

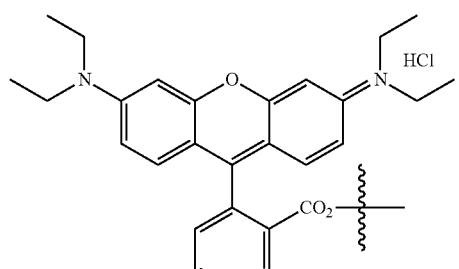

Rhodamines

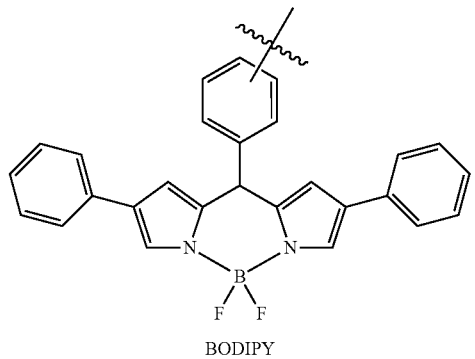

BODIPY

-continued

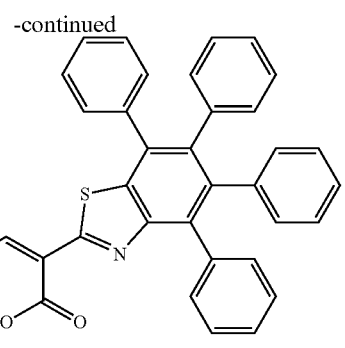

Coumarin

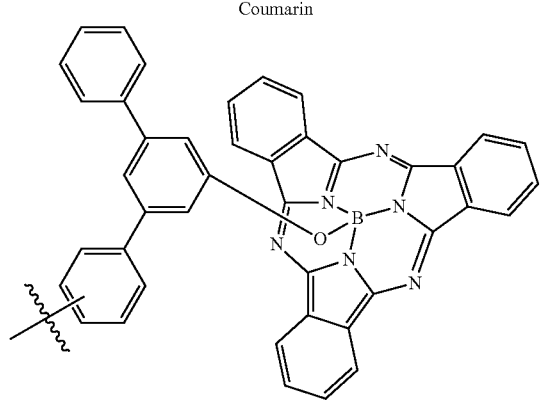

Subphthalocyanine

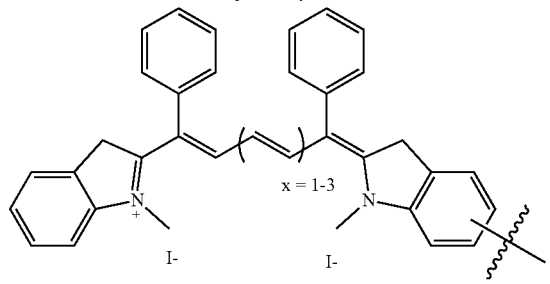

Cyanines

One of skill in the art would understand that the above SEED molecules can be attached to the monomer in multiple different ways. For example, the dye may be attached to the monomer through a phenyl moiety, as represented by the following formula:

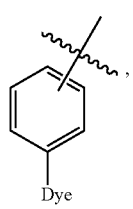

the generic dye (Dye) can be attached to the polymer backbone via the ortho, meta or para positions of any appended phenyl ring (where the phenyl ring is bound to the parent fluorophore to generate the SEE behavior. In a preferred embodiment, the generic dye (Dye) is bound to the polymer backbone via the para-position on the phenyl ring to enable free rotation about the Dye-phenyl-polymer axis. Additionally, specific dye classes may be bound to the polymer backbone via other groups (e.g., carboxylates on fluoresceins, eosins, and rhodamines; aromatic core of coumarins; aromatic end groups of cyanines, etc.).

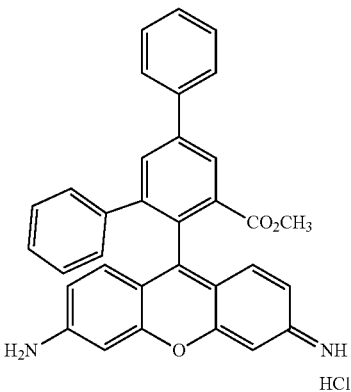

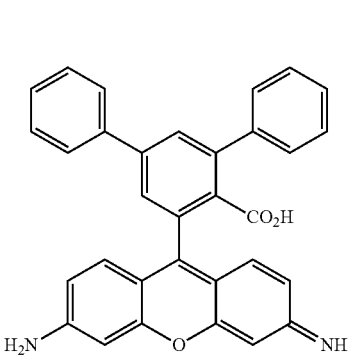

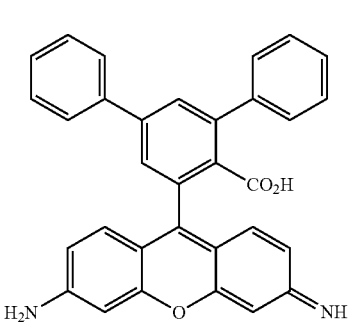

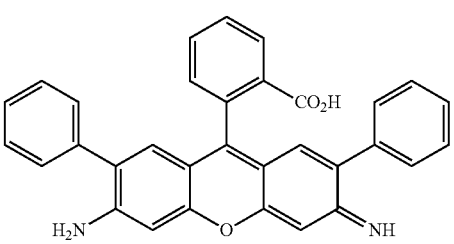

Rhodamine 123 SEED version
Similarly for Rhodamine B and 6G versions

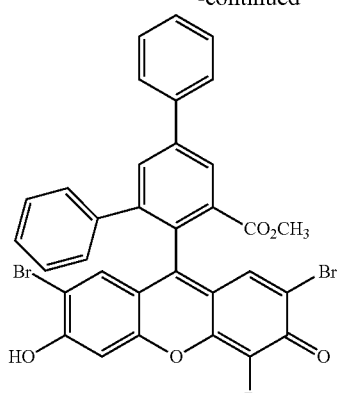
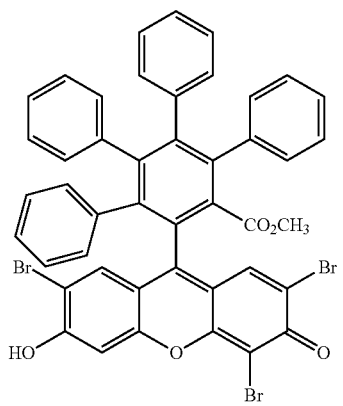
Eosin
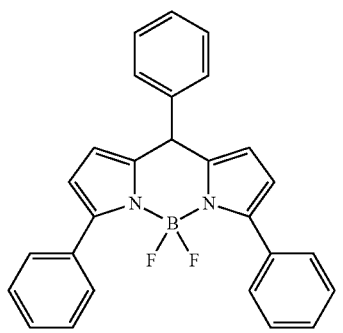
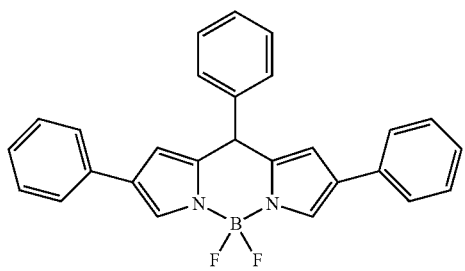
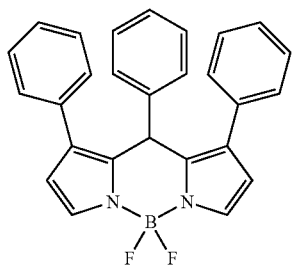
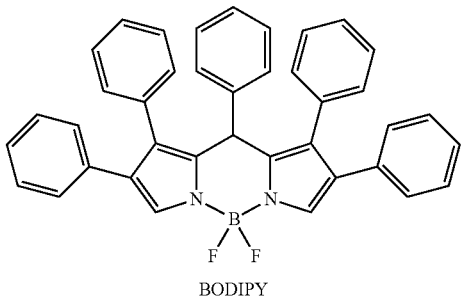
BODIPY
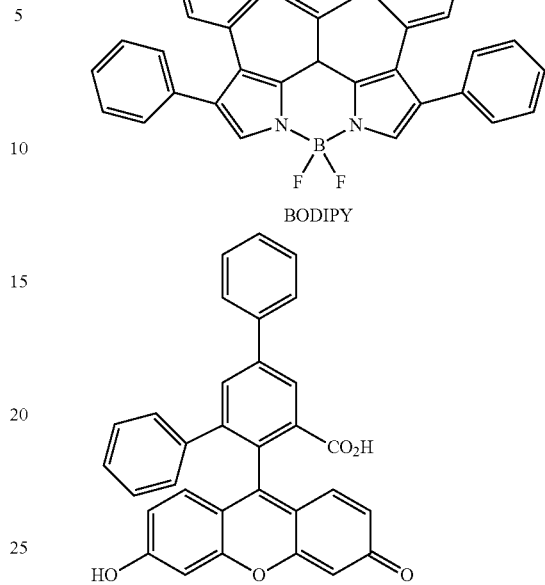
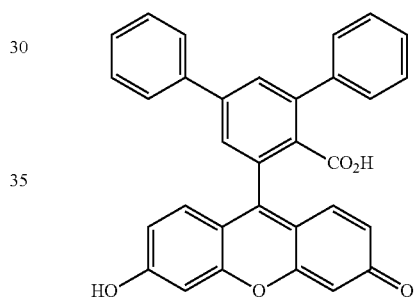
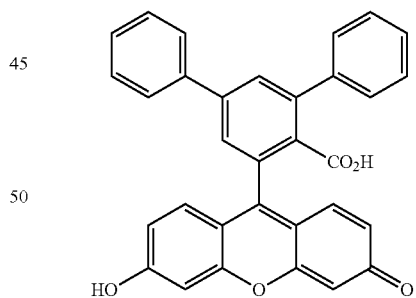
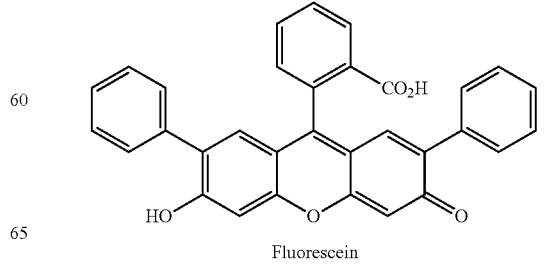
Fluorescein

Representative SEED Clusters
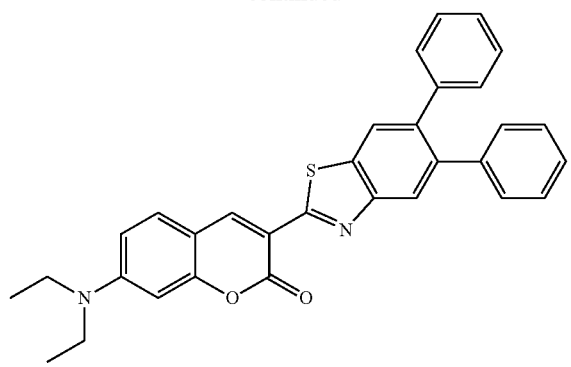
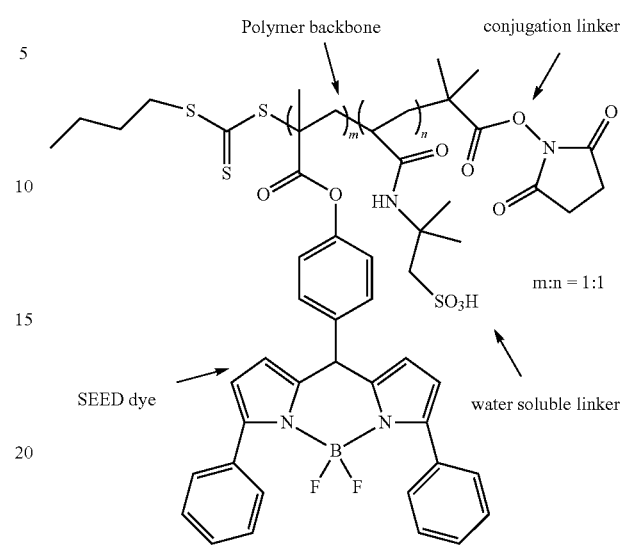
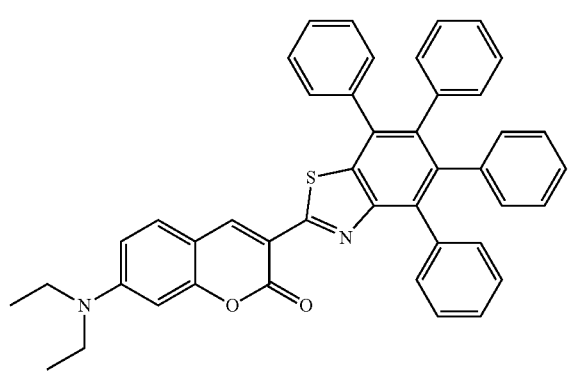
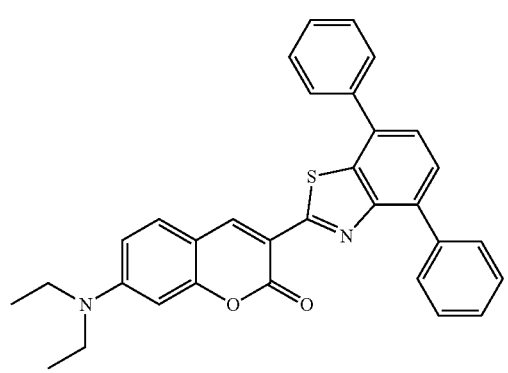
Coumarins
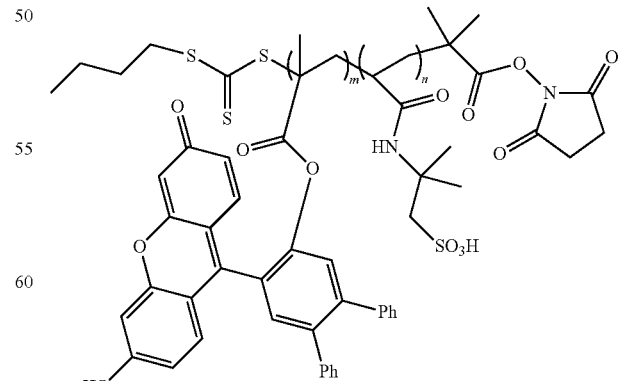
Fluroescein-SEED dye

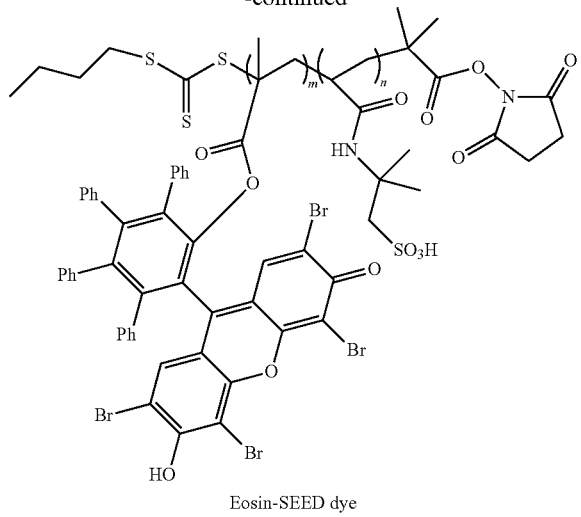

Eosin-SEED dye

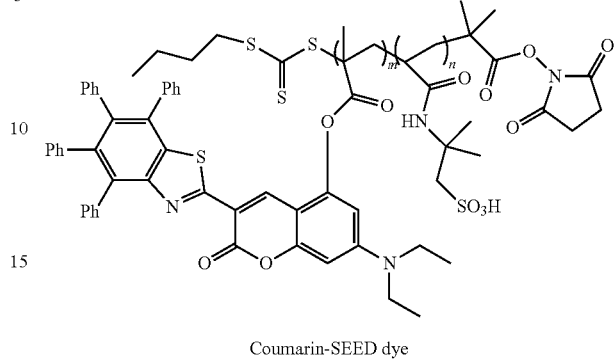

Coumarin-SEED dye

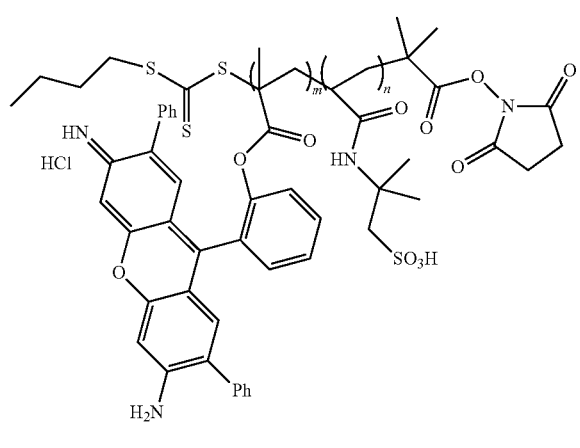

Rhodamine-SEED dye

The present clusters are modular, and additional features can be introduced by attachment of a moiety possessing the desired feature to one or more of the monomer units; or alternatively, the desired feature can be added at one or both of the terminal caps of the polymer; or alternatively; the desired feature can be introduced into the polymer at a combination of one or more monomer units or at one or both of the terminal caps.

In one embodiment, multifunctional monomers are introduced into the polymer backbone, wherein a non-linear polymeric backbone can be generated. For example, ethylene glycol dimethacrylate or trimethylolpropane triacrylate may be used to generate branched or cross-linked polymer chains with other acrylate co-monomers. A representative branched SEED cluster structure based on EGDMA is represented by the following structure:

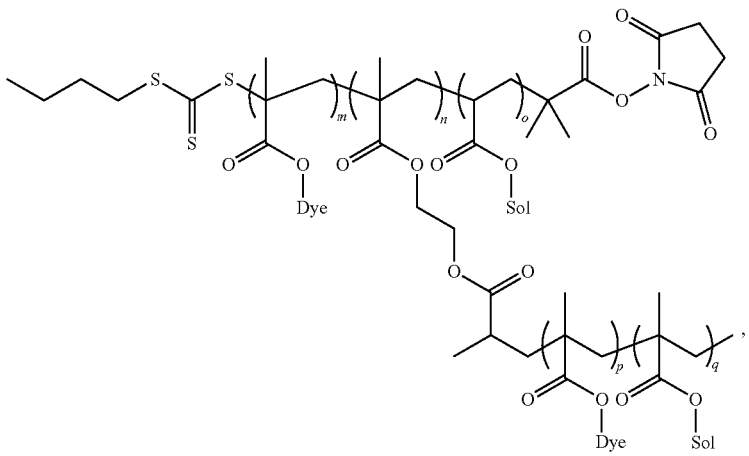

where 'Dye' is a SEED molecule or linked group of SEED molecules, 'Sol' is an aqueous solubilizing group, and Ethylene glycol dimethacrylate (EGDMA) is

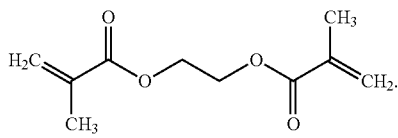

Features that can be incorporated through this modular process include conjugation sites to enable attachment of a biological molecule (e.g., antibody for targeting); or inclusion of moieties that are photostabilizers, sensors, targeting agents, or drug release agents. Any one or a combination thereof these features can be incorporated into the polymer to generate multifunctional dye clusters.

The cluster comprises a site for conjugation to a target. In a specific embodiment, the target is a biological molecule. As such, the cluster includes either a ligand that can bind to a target, or specifically a biological molecule, and/or a targeted binding group that can bind to a target, or specifically a biological molecule. A ligand is biological molecule that specifically binds to another biological molecule. For example, an antibody can be attached to the cluster in order to target binding of the cluster to a specific antigen. Alternatively, or in addition to, the cluster may include a "targeted binding group," which permits the cluster to conjugate with or bind to a target or specifically, a biological molecule, without a ligand present. For example, a targeted binding group either includes a reactive group that can react with a functional group of a biological molecule and/or ligand or, alternatively, includes a functional group that can react with a reactive group on the biological molecule and/or ligand. The reaction between the reactive group and the functional group forms a bond or an interaction between the cluster and the biological molecule, thereby labeling the biological molecule with the SEED cluster.

In at least one embodiment, the site for conjugation is present as a structure -L-Q where L is either a bond or a linker and Q is a targeted binding group. A "targeted binding group" is either a reactive group that reacts with a functional group on the target, or a functional group that reacts with a reactive group on the target, whereby the target becomes covalently or non-covalently attached to the cluster. In a specific embodiment, the target is a biological molecule.

When L is a bond, the targeted binding group Q is attached directly to the polymer. When L is a linker, the targeted binding group Q is separated from the polymeric chain to enhance bio-availability and reactivity.

In at least one embodiment, L is a linker, which may contain 1-60 chain atoms selected from C, N, O, S and P, e.g. a straight chain of 1-30 carbon atoms in which are incorporated one or more N, O, S or P atoms. For example the linker may be —$(CH_2)_x$—

—$((CH_2)_p$—O—$(CH_2)_q)_y$,

—$((CH_2)_p$—CONH—$(CH_2)_q)_y$, or

—$((CH_2)_p$—Ar—$(CH_2)_q)_y$, wherein x is 1-30, preferably 1-10, p is 1-5,
q is 0-5 and
y is 1-5.

Preferred linkers include those that are hydrophilic and uncharged, for example, poly(ethylene glycol) linkers.

In one embodiment, the target bonding group Q may be a group suitable for the formation of a covalent link between the cluster and the target component, such as a reactive or functional group as hereinbefore defined. In the alternative, the target bonding group Q is an affinity tag, for example biotin, desthiobiotin or iminobiotin, and the cluster is bound to the target by non-covalent association.

The conjugation site many include one or more reactive and/or functional groups.

Suitable reactive groups include, but are not limited to, biotin, carboxyl, succinimidyl ester, sulpho-succinimidyl ester, N-hydroxysuccinimidyl ester, cadaverine, isothiocyanate, isocyanate, maleimide, haloacetamide (e.g. bromoacetamide), acid halide, hydrazide, hydrazine, vinylsulphone, dichlorotriazine, phosphoramidite, sulphonyl halide, alkylimido ester, arylimido ester, carbodiimide, anhydrides and acyl azide.

Suitable functional groups include, but are not limited to, primary amine, secondary amine, hydrazine derivatives, hydroxylamine derivatives, pyrazolone, sulphydryl, carboxyl, hydroxyl, thiol, imidazole, thiophosphate, and carbonyl including aldehyde and ketone.

Bioconjugate chemistry is understood by one of skill in the art. Representative descriptions of such technology can be found in Bioconjugate Chemistry: Greg T. Hermanson, "Bioconjugate Techniques, 2nd edition" Academic Press, 2008; and Fluorophores: Joseph Lakowicz, "Principles of Fluorescence Spectroscopy, 3rd edition", Springer, 2006; the entire teachings of both are incorporated herein by reference.

In a specific embodiment, the reactive (or functional) groups selected to be present at the conjugation site are selected based upon the functional (or reactive) group present in the targeted biological molecule. For example, reactive and function group pairing include:

| Reactive Group | Functional Group |
| --- | --- |
| succinimidyl ester; sulpho-succinimidyl ester | primary amine; secondary amine |
| anhydride; acid halide | primary amine; secondary amine; hydroxyl |
| isothiocyanate, vinylsulphone; dichlorotriazine | primary amino groups |
| haloacetamides; maleimide | thiol; imidazole; hydroxyl; amine; thiophosphate |
| carbodiimide | Carboxyl |
| hydrazine, hydrazide | carbonyl including aldehyde and ketone |
| phosphoramidite | hydroxyl |

In another embodiment, the Q may be an affinity tag which is capable of binding specifically and non-covalently with its complementary specific binding partner. Examples of specific binding partner pairs include, but are not restricted to: biotin/avidin, biotin/streptavidin, polyhistidine tag-metal ion complexes with nitrilotriacetic acid (e.g. $Ni^{2+}$: NTA). The complementary specific binding partner may be one component of a labeling complex for detection of a target molecule. Thus, in one preferred labeling format, streptavidin, having four sites of attachment for a biotin label, may be used as a bridge linking a biotin group on the target component with a SEED cluster according to the present invention wherein group Q is biotin, iminobiotin or desthiobiotin. It is to be understood that in the context of the present invention, any two atoms or molecules that possess a specific binding affinity, one for the other, may be employed. Preferred examples of affinity tags are selected from biotin, iminobiotin and desthiobiotin. Additional preferred affinity tags include single-strand DNA/RNA chains complementary for a target sequence of DNA/RNA.

In a specific embodiment, the conjugation site is at the terminal end of the polymer or along the backbone of the polymer, or a combination thereof. In a specific embodiment, the conjugation site is at the terminal end of the polymer. In a specific embodiment, the conjugation site is along the backbone of the polymer.

As used herein, "a biological molecule" includes nucleic acids (e.g. DNA or RNA); nucleotides; nucleotides which contain or are derivatized to contain one or more of an amino, sulfhydryl, carbonyl, hydroxyl; carboxyl and thiophosphate groups; oxy- or deoxy-polynucleic acids which contain or are derivatized to contain one or more of an amino, sulfhydryl, carbonyl, hydroxyl, carboxyl and thiophosphate groups; microbial cells, outer membrane vesicles; viruses; drugs; hormones; cells; cell membranes; toxins; oligonucleotides; aptamers; proteins; protein fragments; antibodies; antigens; antibody fragments (e.g. Fab); carboyhydrates, proteoglycans, lectins, lipids, peptides, small molecules (e.g. biotin, growth factors, hormones, vitamins, therapeutics, drugs); polymer particles or glass beads.

Methods of Using the Clusters

One embodiment of the invention includes a method of labeling a target molecule, comprising the step of incubating the target molecule to be labeled with an amount of the dye clusters under conditions such that the clusters become bound to the target molecule. In a specific embodiment, the target molecule is a biological molecule.

The present invention also relates to the method of labeling a biological molecule comprising the step of contacting a SEED cluster with the biological molecule, wherein the cluster contains at least one of the reactive and/or functional groups and/or affinity tags represented by Q, thereby imparting fluorescent properties to the biological molecule.

In at least one embodiment, the SEED clusters of the present invention may be used for single or multiple labeling and detection of biological molecules as described herein. Thus in a second aspect, there is provided a method for labeling a biological molecule, the method comprising 1) contacting a biological molecule with a cluster of the invention and 2) incubating the cluster with the biological molecule under suitable conditions wherein the cluster binds to and thereby labels the biological molecule.

Methods for the formation of dye conjugates or complexes with target molecules are well known to the skilled person and can be adapted for the formation of complexes of the target biological molecule and the cluster. For example, covalent labeling of proteins is typically performed in an aqueous buffered medium, suitably bicarbonate at pH 9.0, at ambient temperature for a period of typically 1 hour. The reaction is normally carried out in the dark. The labeled protein can be separated from any unreacted cluster by size exclusion chromatography, for example using Sephadex™ as the stationary phase and phosphate buffer, pH 7.0 as the eluant. For multiple labeling of a target biological molecule, the ratio of the amount or concentration of cluster to target material should be adjusted accordingly.

In addition to the foregoing one-step labeling process, the present invention also relates to two-step labeling processes in which, in a first step, a cluster according to the present invention binds to, and thereby labels a primary target molecule, such as an antibody, protein, DNA probe, etc. In the second step of the labeling process, the fluorescently labeled primary target molecule is then used as a probe for detection of a secondary target molecule, such as an antigen for which the antibody is specific.

The clusters of the present invention can also be used to determine the concentration of a particular protein or other component in a system. If the number of reactive groups on a protein which can react with the cluster is known, the fluorescence per molecule can be known and the concentration of these molecules in the system can be determined by the total fluorescence intensity of the system. This particular method can be used to measure the concentration of various labeled analytes using microtitre plate readers or other known immunofluorescence detection systems. The concentration of fluorescently labeled material can also be determined using, for example, fluorescence polarization detection instruments.

The clusters of the present invention may also be used in a detection method wherein a plurality of the clusters are covalently attached to a plurality of different primary target molecules, such as antibodies, each primary target molecule being specific for a different secondary target molecule, such as an antigen, in order to identify each of a plurality of secondary target molecules in a mixture of secondary target molecules. According to this method of use, each of the primary target molecules is separately labeled with a cluster having a different light absorption and emission wavelength characteristic, compared with the cluster molecules used for labeling the other primary target molecule(s). The labeled primary target molecules are then added to the preparation containing the secondary target molecule, such as antigens, and the primary target molecules are allowed to attach to the respective secondary target molecule for which they are selective. Any unreacted cluster may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochromators to select the excitation wavelength and to select the wavelengths of fluorescence emission is next employed to determine the intensity of the emission at the wavelengths corresponding to the fluorescent compounds utilized, the intensity of fluorescence indicating the quantity of the secondary target molecule which has been bound with a particular labeled primary target molecule. Known techniques for conducting multi-parameter fluorescence studies include, for example, multiparameter flow cytometry. In certain cases, a single wavelength of excitation can be used to excite fluorescence from two or more materials in a mixture where each fluoresces at a different wavelength and the quantity of each labeled species can be measured by detecting its individual fluorescence intensity at its respective emission wavelength. If desired, a light absorption method can also be employed.

The detection method of the present invention can be applied to any system in which the creation of a fluorescent primary target molecule is possible. For example, an appropriately reactive fluorescent compound can be conjugated to a DNA or RNA fragment and the resultant conjugate then caused to bind to a complementary target strand of DNA or RNA. Appropriate fluorescence detection equipment can then be employed to detect the presence of bound fluorescent conjugates.

Synthetic Methods.

Representative Syntheses of Different Classes of SEED Dyes.

The following schemes are representative synthetic schemes for the preparation of SEED dyes. Variants of the representative SEED dyes can be prepared by altering the starting materials or reaction conditions depicted in each scheme.
Scheme 1: BODIPY
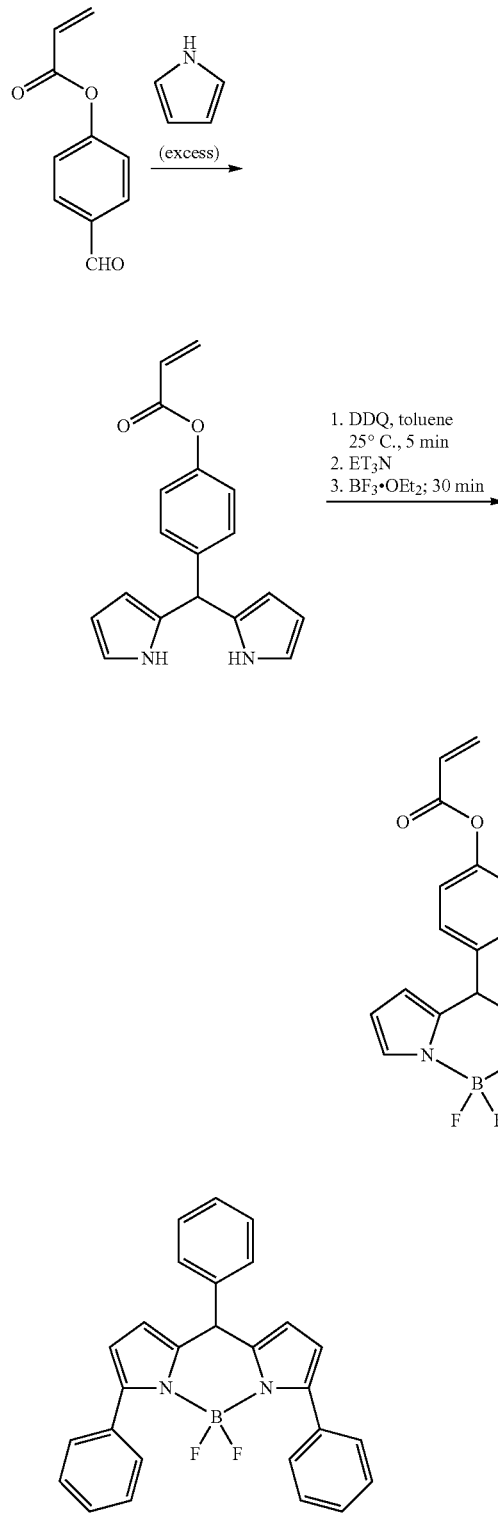
Scheme 2: Coumarin.
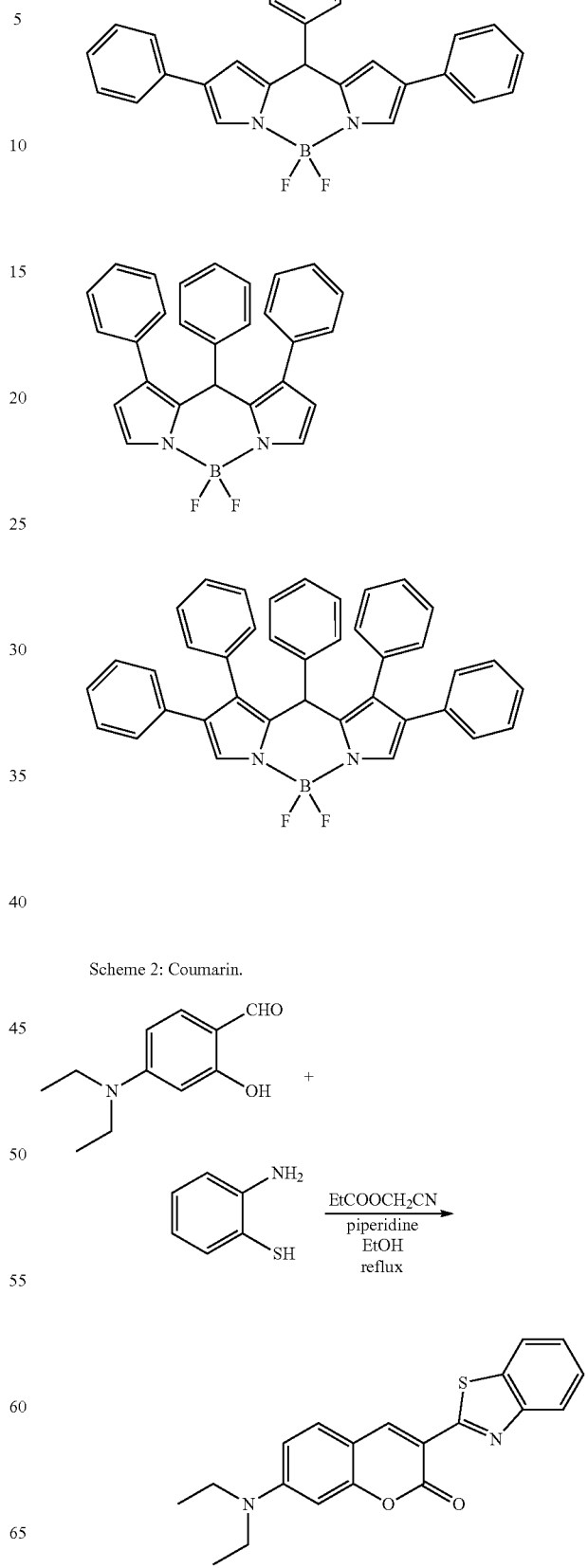

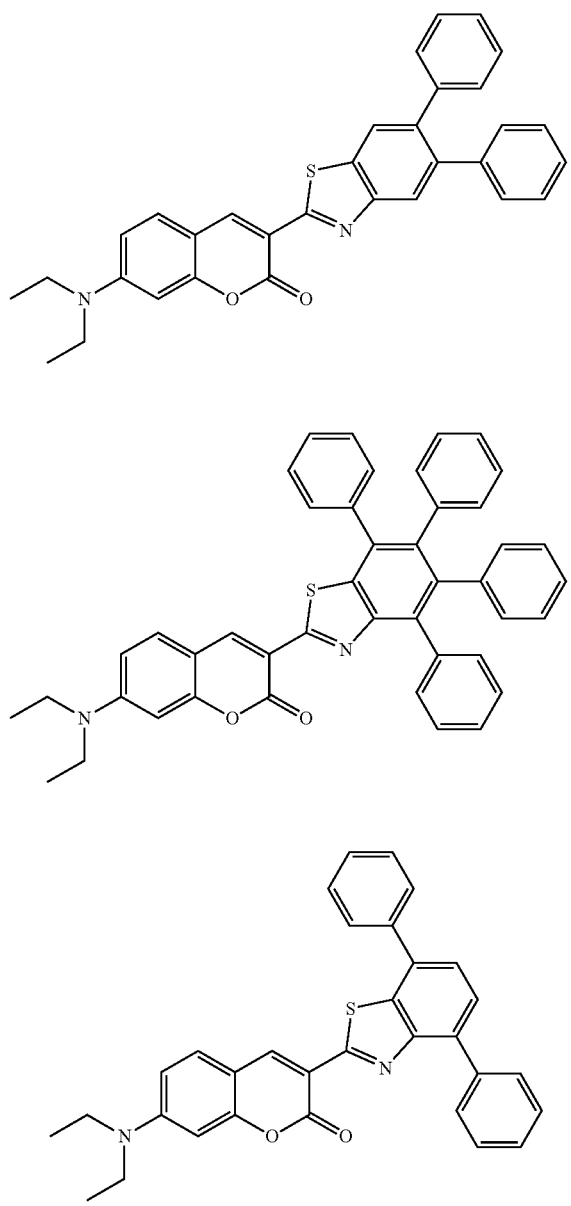
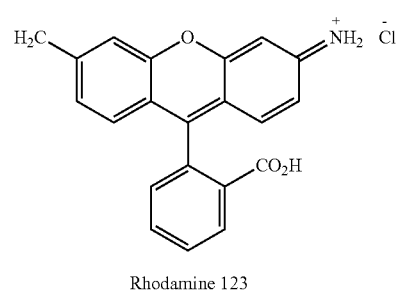
Rhodamine 123
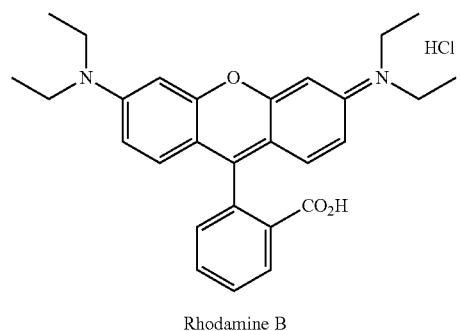
Rhodamine B
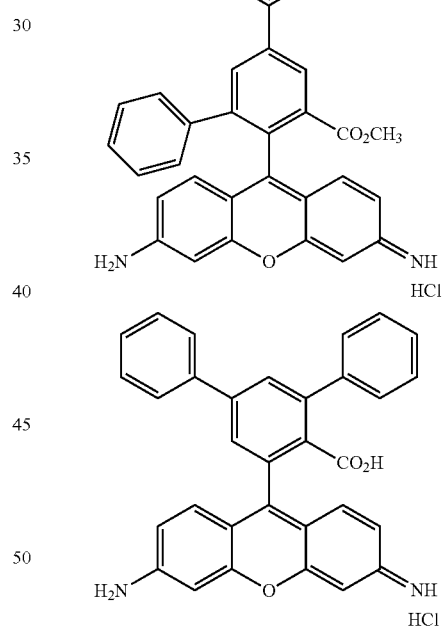
Rhodamine 123 SEED version
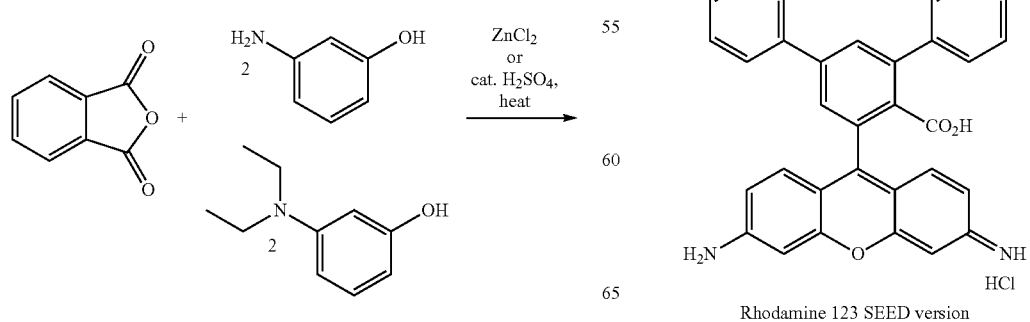
Scheme 3: Rhodamine.

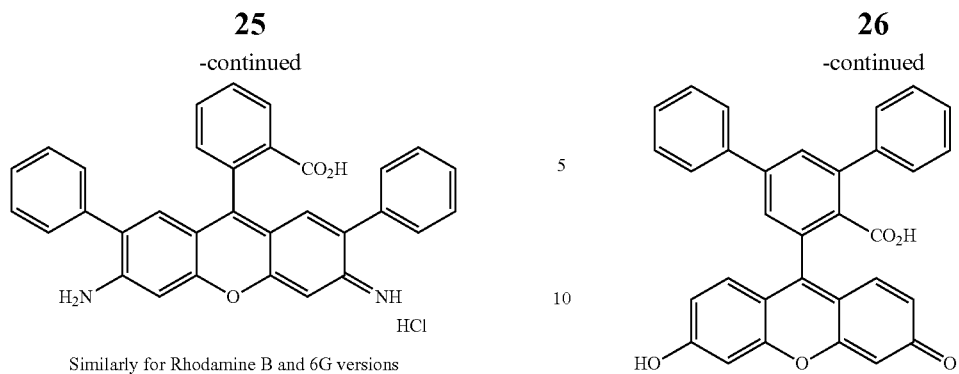
Similarly for Rhodamine B and 6G versions
Scheme 4: Fluorescein.
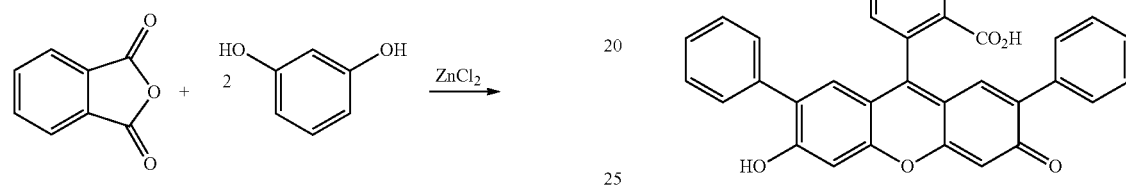
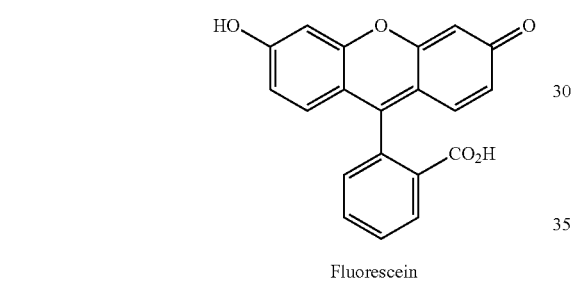
Fluorescein
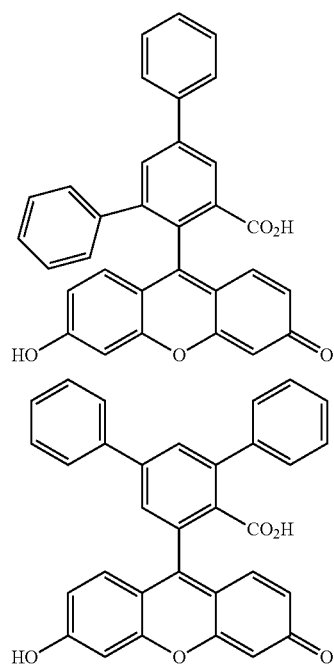
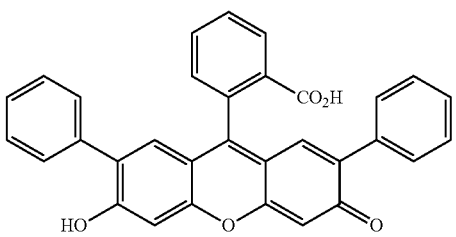
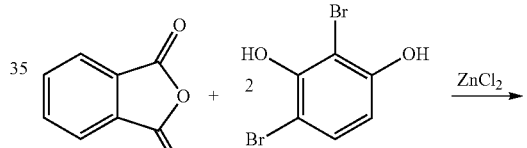
Scheme 5: Eosin
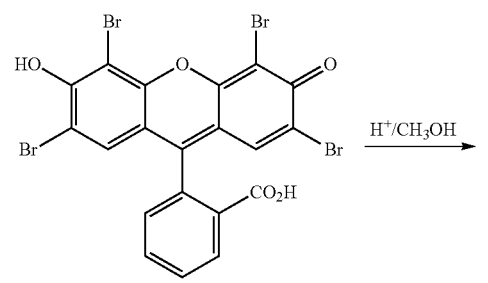
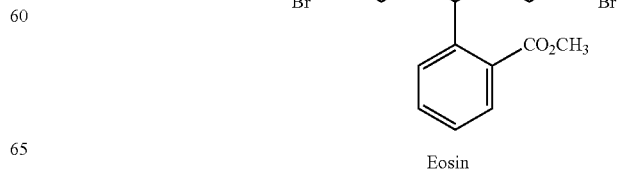
Eosin

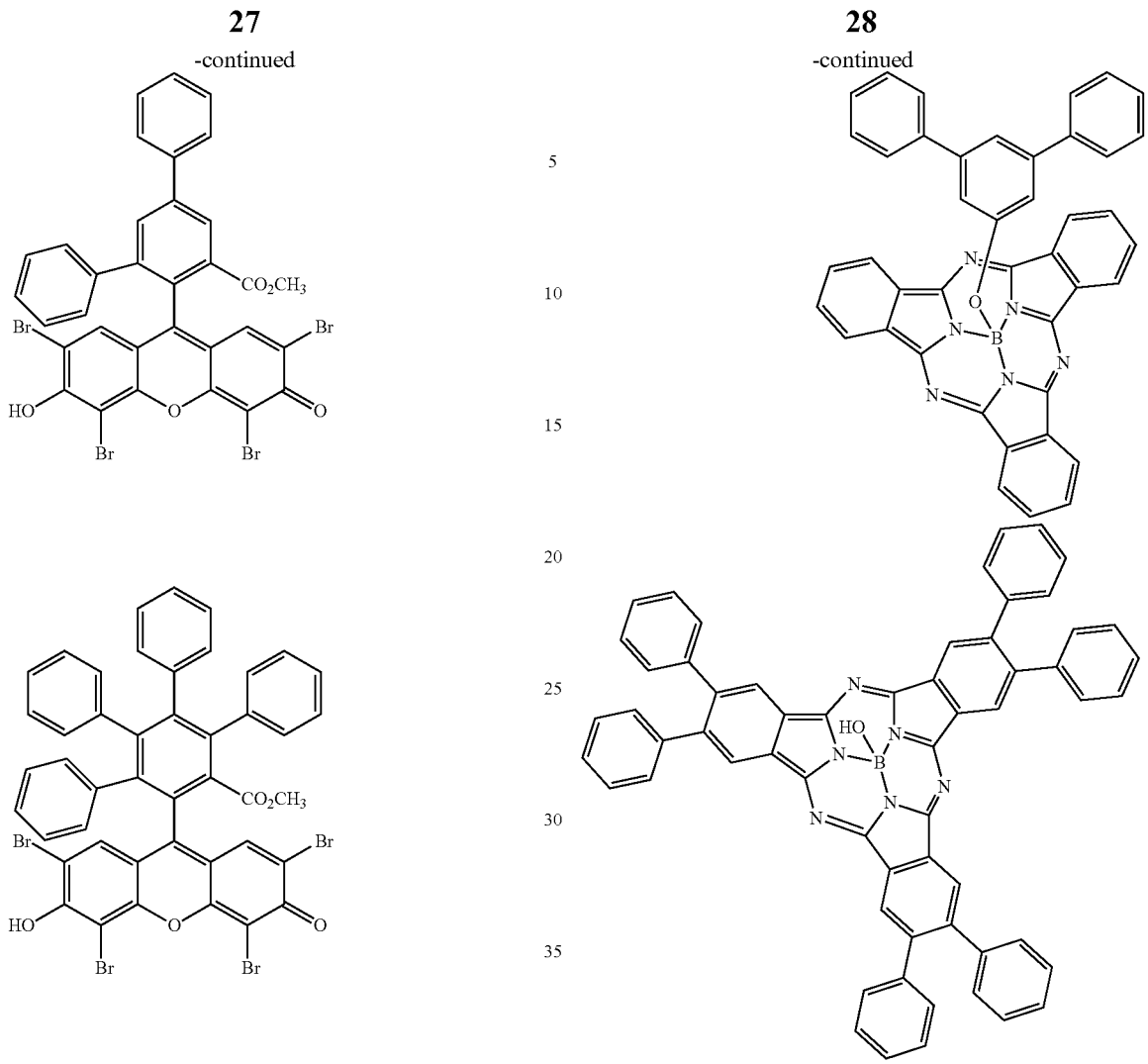

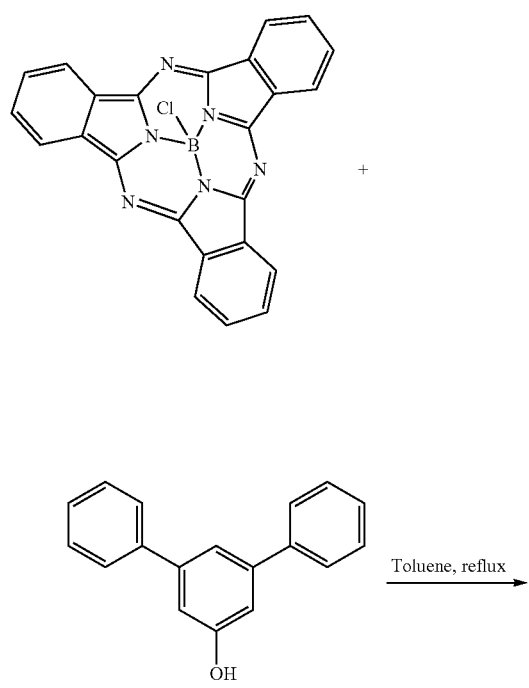

Scheme 6: Subphthalocyanines

Attachment of the SEED Molecules to the Cluster or Polymer.

The SEED molecule can be attached to the cluster in two ways. In method A, a monomer unit with a SEED molecule appended to it is used to form the cluster. In Method B, the SEED molecule may be added to the pre-formed polymeric chain through a reactive moiety on both the SEED molecule and the polymer chain.

Synthesis of the Conjugation Site(s).

The synthesis of clusters that include a conjugation site can also be synthesized in a variety of ways. In one scheme, the reactive (or functional) group may be introduced as a co-monomer to the polymer chain as it is forming, and thus a single polymer may incorporate multiple reactive (or functional) groups. In this embodiment, the monomer must comprise two functionalities, first, a chemistry capable of reaction with the backbone as it polymerizes (e.g, acrylate, methacrylate, epoxide, etc.) to form the polymer, as well as a second reactive group which is selected from the list of reactive (or functional) groups defined herein.

Alternatively, the conjugation site may be introduced as a chain-terminating agent, wherein the propagating chain is terminated upon reaction with the reactive (or functional) group of the conjugation site. This embodiment would ensure that each polymer which contains a reactive (or functional) group contains only one reactive (or functional) group, which is of importance in preventing cross-linking reactions wherein a single polymer reacts with multiple biomolecules which can lead to inactivation or other unwanted or unexpected behavior of the biological molecule in use.

Alternatively, a chain initiator containing the reactive group can be used in the synthesis. Similarly, using an appropriate controlled radical polymerization technique such as reversible addition-fragmentation chain transfer (RAFT) allows the controlled incorporation of a reactive (or functional) group via an appropriately modified dithioester. Other controlled radical polymerization techniques may also be employed such as atom transfer radical polymerization (ATRP). An advantage to the use of a controlled radical polymerization technique is lower polydispersity compared to traditional free radical polymerizations. For other polymerization techniques, such as anionic polymerizations, the reactive species may also be incorporated via an appropriately chosen initator.

Bioconjugate chemistry is understood by one of skill in the art. Representative descriptions of such technology can be found in Bioconjugate Chemistry: Greg T. Hermanson, "Bioconjugate Techniques, 2nd edition" Academic Press, 2008; and Fluorophores: Joseph Lakowicz, "Principles of Fluorescence Spectroscopy, 3rd edition", Springer, 2006; the entire teachings of both are incorporated herein by reference.

EXEMPLIFICATION

Example 1

Synthesis of Para-hydroxylated Tetraphenylethylene (TPE-OH)

A literature procedure reported in *J. Org. Chem.*, 2005, 70, 3765 was followed for making this compound. Diphenyl acetylene (4 g, 22.5 mmol) was taken in a 250 mL flame-dried round bottom flask and p-iodophenol (14.8 g, 67.5 mmol) and phenyl boronic acid (8.16 g, 67.5 mmol) were added and dissolved in 100 mL of 80/20 DMF/$H_2O$ (v/v) which was followed by addition of potassium hydrogen carbonate (6.7 g, 67.5 mmol). This reaction mixture was stoppered and nitrogen purged while stirring for 30 minutes. After 30 minutes, $PdCl_2(PhCN)_2$ catalyst (0.086 g, 0.22 mmol) was added and the reaction mixture was stirred overnight at room temperature. The reaction mixture was diluted with 200 mL water and the organic compounds were extracted into 200 mL of methylene chloride (twice) and dried over $MgSO_4$. The only by-product (p-hydroxybiphenyl) was removed by hexane wash as the TPE-OH was only sparingly soluble in hexane. 3.6 g of TPE-OH was isolated after purification.

Example 2

Synthesis of TPE-Methacrylate Monomer (TPE-M-monomer)

TPE-OH (2 g, 6.57 mmol) was taken into a 250 mL flame-dried round bottom flask and triethylamine (0.73 g, 7.2 mmol) was added. This mixture was dissolved in 100 mL of methylene chloride and the flask was stoppered and nitrogen purged for 30 minutes. Later, methacryloyl chloride (0.718 g, 6.9 mmol) was dissolved in 30 mL of methylene chloride and added drop-wise into the reaction mixture which was placed in an icebath. After drop-wise addition for over 30 minutes, the reaction mixture was allowed to warm to room temperature and was stirred overnight. The reaction was quenched with 100 mL water and extracted twice with 100 mL of methylene chloride and the organic layer was dried over $MgSO_4$. The product was purified using column chromatography (Silica), with eluent Ethyl Acetate:Hexane=10:90. The first eluted fraction from column chromatography was the product. Yield: 1.3 g.

Example 3

Synthesis of TPE-M-polymer

TPE-M-monomer (30 wt % in toluene; 0.3 g in 0.7 g toluene) was taken a single neck round bottom flask, stoppered and nitrogen purged for 30 minutes. After removing as much oxygen as possible, 4 mole % of azobisisobutyronitrile (AIBN) was added and a cold-water condenser was fitted to the flask which was refluxed at 80° C. overnight. To quench the reaction, the reaction mixture was diluted with 5 mL methylene chloride. This reaction mixture was added drop-wise to 20 mL methanol in a beaker while stirring the solution. The polymer precipitated and the solvent was filtered to isolate 0.2 g of the polymer.

Example 4

Synthesis of TPE-M-polymer-water Soluble-1

TPE-M-monomer (30 wt % in toluene; 0.3 g in 0.7 g toluene) was taken a single neck round bottom flask, stoppered and nitrogen purged for 30 minutes. To this mixture, 20 mol % of APES-10 (ammonium allylpolyethoxy (10) alkoxylated acrylate) was added as the water solubilizing monomer. After removing all possible oxygen, 4 mole % of AIBN was added and a cold water condenser was fitted to the flask while the reaction mixture was refluxed at 80° C. overnight. Upon completion, the reaction mixture was diluted with 5 mL methylene chloride. This mixture was then added drop-wise to 20 mL methanol in a beaker while stirring the solution. The polymer precipitated and the solvent was filtered to isolate 0.2 g of the polymer.

Example 5

Additional Water Soluble TPE-M-polymers

A similar procedure was used to make different water soluble versions of the TPE-M-polymer by changing the mol % of APES-10 from 20-67 mol % with increasing water solubility. Also, a similar procedure was followed to make a second TPE-M-polymer in which 2-acrylamidomethylpropane sulfonic acid was used as the water solubilizing monomer instead of APES-10. This monomer was tested at 50 mol % ratio and was found to exhibit better water solubilization than APES-10.

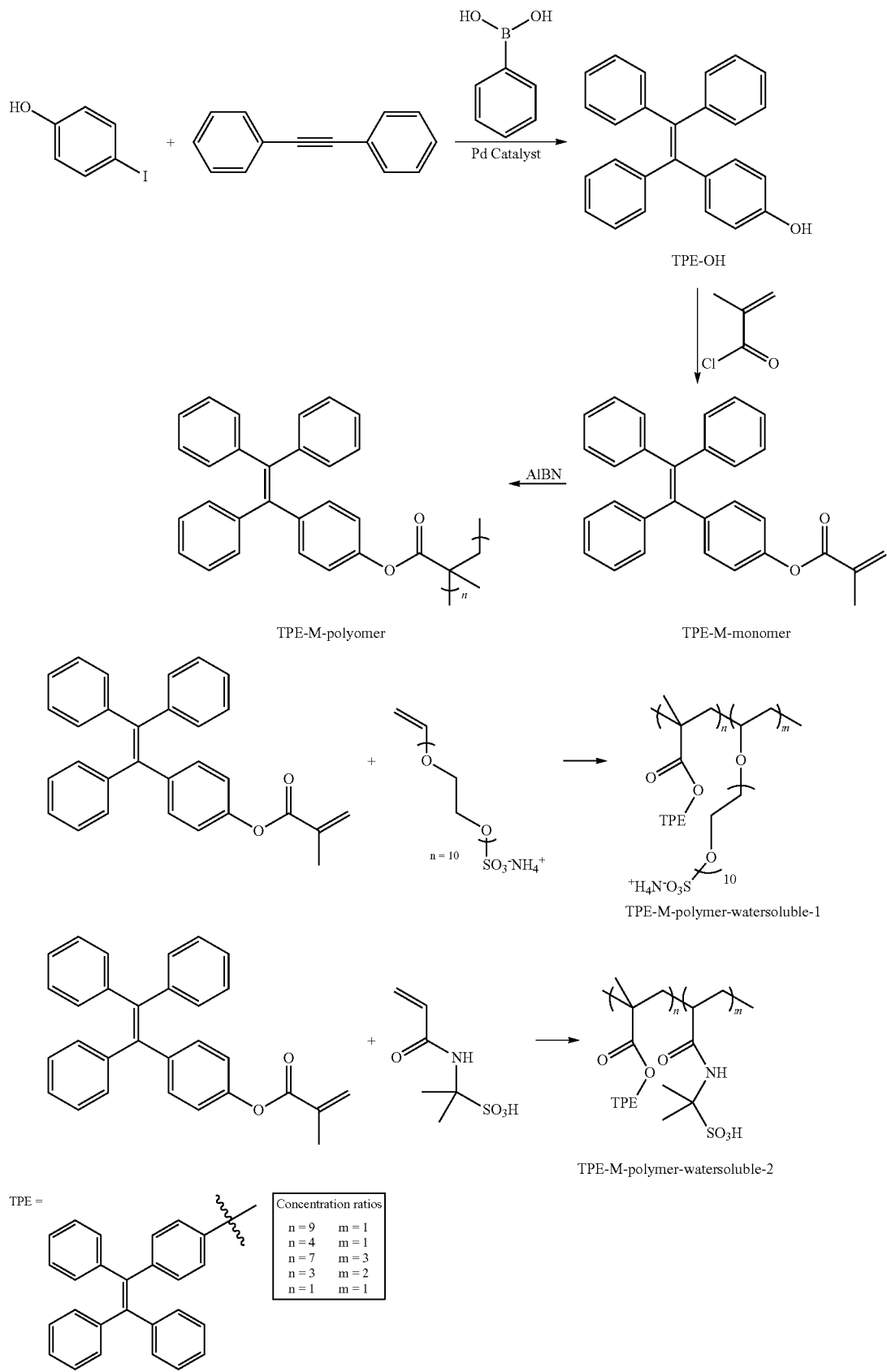

Example 6

Additional Water Soluble TPE-M-polymers

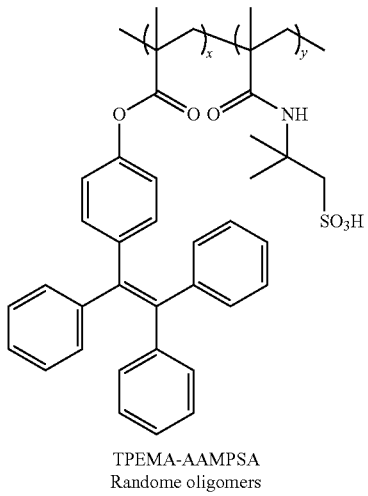

TPEMA-AAMPSA
Randome oligomers

The above water-soluble SEED cluster was synthesized. Specifically, a tetraphenylethene methacrylate (TPEM) monomer was reacted with 2-acrylamido-2-methylpropane-sulfonic acid (AMPSAA) in a 1:1 molar ratio with azobisisobutyronitrile (AIBN) as a radical initiator added at a 0.04:1 mol ratio of AIBN:TPEM. This mixture was refluxed in N-methylpyrrolidone (NMP), under nitrogen at 80° C. for 12 hours, after which crude reaction mixture was poured into a stirring acetone solution to precipitate the dye clusters. The precipitate was vacuum filtered to remove the organics and the polymer was dried under house vacuum.

Example 7

Fluorescence of Water Soluble TPE-M-polymers

For absorbance/fluorescence studies, the dye clusters were initially dissolved in dimethylsulfoxide (DMSO) at a concentration of 10.8 mg/ml. This solution was diluted into water to generate aqueous solutions at concentrations of 5.4 μg/ml to 108 μg/ml in water. The high concentration sample was filtered (0.2 micron Teflon membrane) and its hydrodynamic size was measured on a Brookhaven Dynamic Light Scattering apparatus. The size of the initial batch of dye clusters was found to be 18 nm in diameter (this size is approximate, due to the low scattering cross-section of the clusters in solution).

Figure 2:
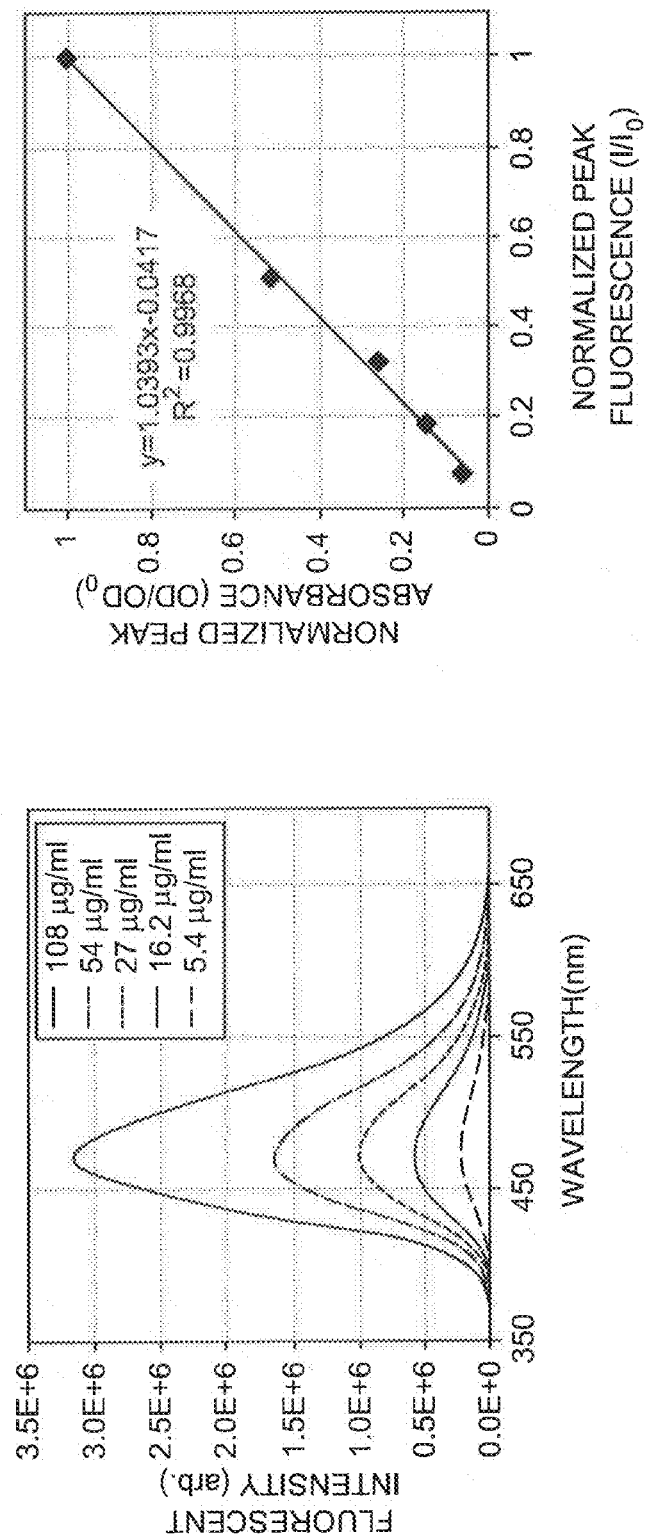
FIG. 2 is a fluorescence spectrum for water soluble chain-bound SEED clusters (left), and a comparison of normalized absorbance (peak) and emission (peak) showing a linear correlation between concentration and emission indicating that the SEED effect is occurring among the molecules bound to each cluster and without concentration-mediated quenching at high concentration.

To demonstrate the dye cluster behavior, we studied the relationship between concentration (as measured by absorbance) and fluorescent emission. For un-bound AIE dyes, this relationship is highly non-linear because the quantum yield of fluorescence is dependent on the local environment surrounding the dye, with very low quantum yield for freely diffusing dye, a sigmoidal increase in intensity as dyes begin to aggregate and a plateau for high concentrations where dye molecules are completely aggregated and all dye molecules are emitting at peak quantum yield. For chain-bound dye molecules, this relationship is expected to be linear, due to the fact that the dye molecules are 'pre-aggregated' by their molecular proximity on the chain, thus their environment does not change with concentration, nor will their quantum yield of fluorescence. Our results showed a linear correlation between normalized absorbance and normalized emission ($R^2=0.999$ for 5 concentrations, slope=1.039, FIG. 2).

Equivalents

Those skilled in the art will recognize, or be able to ascertain using no more than routine experimentation, numerous equivalents to the specific procedures described herein. Such equivalents are considered to be within the scope of the present invention and are covered by the following claims.

We claim:

1. A cluster comprising:
   a 3 to 100 monomer unit polymer backbone, comprising two or more optionally substituted monomer units;
   a solubilizing agent;
   a conjugation site; and
   a multiplicity of sterically enhanced emission dye molecules disposed along the polymer backbone.

2. The cluster of claim 1, wherein at least two sterically enhanced emission dyes are attached to one or more of the monomer units.

3. The cluster of claim 1, wherein the polymer is comprised of 10 to 40 monomer units.

4. The cluster of claim 1 wherein the hydrodynamic diameter of the cluster is less than 100 nm.

5. The cluster of claim 4, wherein the hydrodynamic diameter of the cluster is between 2 and 15 nm.

6. The cluster of claim 1, wherein each monomer unit is formed from a group independently selected from an alkenyl, an acrylate, an ether, an amine, or a combination thereof.

7. The cluster of claim 6, wherein the monomer unit is formed from the group selected from acrylate, methylacrylate, vinyl, urethane, epoxide, or a combination thereof.

8. The cluster of claim 1, wherein the solubilizing agent is selected from, oligo(ethylene glycol), oligosaccharides, cationically charged groups, anionically charged groups, zwitterionically charged groups, or combinations thereof.

9. The cluster of claim 1, wherein each sterically enhanced emission dye is independently attached to the one or more monomer units either directly or through a linker.

10. The cluster of claim 1, wherein each sterically enhanced emission dye within the cluster is the same.

11. The cluster of claim 1, wherein at least two or more different sterically enhanced emission dyes are within the cluster.

12. The cluster of claim 11, wherein the different sterically enhanced emission dyes have different absorption and/or emission wavelengths.

13. The cluster of claim 12, wherein the wavelength is between 300 and 850 nm.

14. The cluster of claim 13, wherein the molar ratio of different sterically enhanced emission dyes in each cluster is controlled.

15. The cluster of claim 1, wherein each sterically enhanced emission dye is independently selected from the group consisting of rhodamines, fluoresceins, eosins, cyanines, boron dipyridyls, xanthenes, carbopyrinins, acridiniums, benzopyriniums, and acridiniums.

16. The cluster of claim 1, wherein the molar ratio of the sterically enhanced emission dye and the solubilizing agents in each cluster is controlled.

17. The cluster of claim 1, wherein the conjugation site is a reactive group selected from biotin, carboxyl, succinimidyl ester, sulpho-succinimidyl ester, N-hydroxysuccinimidyl ester, cadaverine, isothiocyanate, isocyanate, maleimide, haloacetamide acid halide, hydrazide, hydrazine, vinylsulphone, dichlorotriazine, phosphoramidite, sulphonyl halide, alkylimido ester, arylimido ester, carbodiimide, anhydrides or acyl azide; or a functional group selected from a primary amine, secondary amine, hydrazine derivatives, hydroxylamine derivatives, pyrazolone, sulphydryl, carboxyl, hydroxyl, thiol, imidazole, thiophosphate, or carbonyl including aldehyde or ketone.

18. The cluster of claim 17, wherein the conjugation site is at the terminal end of the polymer or along the backbone of the polymer.

19. The cluster of claim 17, wherein the conjugation site can bind to a target.

20. The cluster of claim 19, wherein the target is a biological molecule.

21. A sustained emission high density luminescent cluster comprising:
- a 3 to 100 monomer unit polymer backbone comprising two or more optionally substituted monomer units;
- a solubilizing agent;
- a conjugation site; and
- a multiplicity of sterically enhanced emission dye molecules disposed along the polymer backbone such that rotational decay is suppressed and emission is sustained.

* * * * *